US009763894B2

(12) United States Patent
Martin et al.

(10) Patent No.: US 9,763,894 B2
(45) Date of Patent: Sep. 19, 2017

(54) INFLAMMATION THERAPY

(75) Inventors: Billy R. Martin, Richmond, VA (US); Mohamad Imad Damaj, Richmond, VA (US); Martin W. Adler, Philadelphia, PA (US); Ronald F. Tuma, Philadelphia, PA (US); Ming Zhang, Philadelphia, PA (US); Anu Mahadevan, Woburn, MA (US); Raj K. Razdan, Woburn, MA (US)

(73) Assignees: Virginia Commonwealth University, Richmond, VA (US); Organix, Inc., Woburn, MA (US); Temple University, Philadelphia, PA (US)

( * ) Notice: Subject to any disclaimer, the term of this patent is extended or adjusted under 35 U.S.C. 154(b) by 1683 days.

(21) Appl. No.: 11/950,456

(22) Filed: Dec. 5, 2007

(65) Prior Publication Data

US 2008/0139635 A1 Jun. 12, 2008

Related U.S. Application Data

(60) Provisional application No. 60/872,794, filed on Dec. 5, 2006.

(51) Int. Cl.
*A01N 31/08* (2006.01)
*A61K 31/05* (2006.01)
*A61K 31/045* (2006.01)
*A61K 31/015* (2006.01)
*A61K 31/09* (2006.01)
*A61K 31/4164* (2006.01)

(52) U.S. Cl.
CPC .......... *A61K 31/045* (2013.01); *A61K 31/015* (2013.01); *A61K 31/09* (2013.01); *A61K 31/4164* (2013.01)

(58) Field of Classification Search
None
See application file for complete search history.

(56) References Cited

U.S. PATENT DOCUMENTS

| | | | |
|---|---|---|---|
| 4,092,344 | A | 5/1978 | Matsumoto |
| 4,102,902 | A | 7/1978 | Archer et al. |
| 4,282,248 | A | 8/1981 | Mechoulam et al. |
| 4,707,559 | A | 11/1987 | Mechoulam et al. |
| 4,758,597 | A | 7/1988 | Martin et al. |
| 5,434,295 | A | 7/1995 | Mechoulam et al. |
| 6,274,635 | B1 | 8/2001 | Travis |
| 6,563,009 | B1 | 5/2003 | Kunos et al. |
| 6,630,507 | B1 | 10/2003 | Hampson et al. |
| 6,903,137 | B2 * | 6/2005 | Fride et al. .......... 514/719 |
| 7,179,800 | B2 | 2/2007 | Martin et al. |
| 2005/0159449 | A1 * | 7/2005 | Martin et al. .......... 514/317 |

FOREIGN PATENT DOCUMENTS

WO  WO 01/28329 A1  4/2001
WO  WO 01/95899 A2  12/2001

OTHER PUBLICATIONS

Eltzschig et al. (British Medical Bulletin, vol. 70, pp. 71-86; 2004).*
Elliott et al. (European Journal of Pharmacology, vol. 386, pp. 313-315; 1999).*
Galinsky et al. ["Basic Pharmacokinetics and Pharmacodynamics." in: Remington: The Science and Practice of Pharmacy (Baltimore, Lippincott Williams & Wilkins, 2006), p. 1171].*
Beech et al. (Journal of Cerebral Blood Flow and Metabolism, vol. 21, pp. 683-689; 2001).*
Di Filippo et al. (J. Leukoc. Biol., vol. 75, pp. 453-459; 2004).*
Lagneux et al. (British Journal of Pharmacology, vol. 132, pp. 793-796; 2001).*
Wiley et al. "Resorcinol Derivatives: A Novel Template for the Development of Cannabinoid CB1/CB2 and CB2-Selective Agonists", J.Pharmacol.Exp.Ther., 2002, vol. 301, No. 2, pp. 679-689.*
Rivers-Auty et al. "The cannabinoid CB2 receptor agonist GW405833 does not ameliorate brain damage induced by hypoxia-ischemia in rats", Neurosci.Lett., 2014, vol. 569, lines 104-109.*
Zhang et al. "Evaluation of spinal cord injury animal models", Neural Regen. Res., 2014, vol. 9, No. 22, pp. 2008-2012.*
Adams, et al., "Evaluation of Cannabinoid Receptor Binding and in Vivo Activities for Anandamide Analogs," *J. Pharmacology and Exp. Ther.*, 273(3):1172-1181, 1995.
D'Ambra, et al., "Conformationally Restrained Analogues of Pravadoline: Nanomolar Potent, Enantioselective, (Aminoalkyl)indole Agonists of the Cannabinoid Receptor," *J. Med. Chem.*, 35:124-135, 1992.
Aung, et al., "Influence of the N-1 Alkyl Chain Length of Cannabimimetic Indoles Upon $CB_1$ and $CB_2$ Receptor Binding," *Drug Alcohol Depend.*, 60:133-140, 2000.
Baek, et al., "Boron Trifluoride Etherate on Alimina—A Modified Lewis Acid Reagent. An Improved Synthesis of Cannabidiol." *Tetrahedron Letters*, 26(8):1083-1086, 1985.
Baek, et al., "Boron Trifluoride Etherate on Alumina—A Modified Lewis Acid Reagent (VI). Synthesis of 2'-(1-Acetoxymethyl-1-cyclohexen-3-yl)-5'-alkylresorcinol Diacetate Derivatives," *Bull. Korean Chem. Soc.* 15(6): 507-508, 1994.
Baek, "Simplified Cannabidiols. Part 1. Boron Trifluoride-Diethyl Ether on Alumina: A Modified Lewis Acid Reagent. Friedel-Crafts Alkylation of 5-Alkylresorcinols with Cyclic Allylic Alcohols," *J. Chem. Research (S)*: 451, 1994.
Bradford, "A Rapid and Sensitive Method for the Quantitation of Microgram Quantities of Protein Utilizing the Principle of Protein-Dye Binding," *Anal Biochem*, 72: 248-254, 1976.
Compton et al., "Cannabinoid Structure-Activity Relationships: Correlation of Receptor Binding and in Vivo Activities," *Pharmacol. Exp. Ther.*, 265(1): 218-226, 1993.

(Continued)

*Primary Examiner* — Jeffrey S Lundgren
*Assistant Examiner* — Stephanie Springer
(74) *Attorney, Agent, or Firm* — RatnerPrestia

(57) ABSTRACT

A method is provided for treating a patient in need of therapy for central nervous system inflammation comprising administering to that patient a therapeutically effective amount of a cannabinoid agonist having efficacy at the $CB_2$ receptor but having substantially no efficacy at the $CB_1$ receptor at that amount.

4 Claims, 14 Drawing Sheets

(56) References Cited

OTHER PUBLICATIONS

Figure 1:
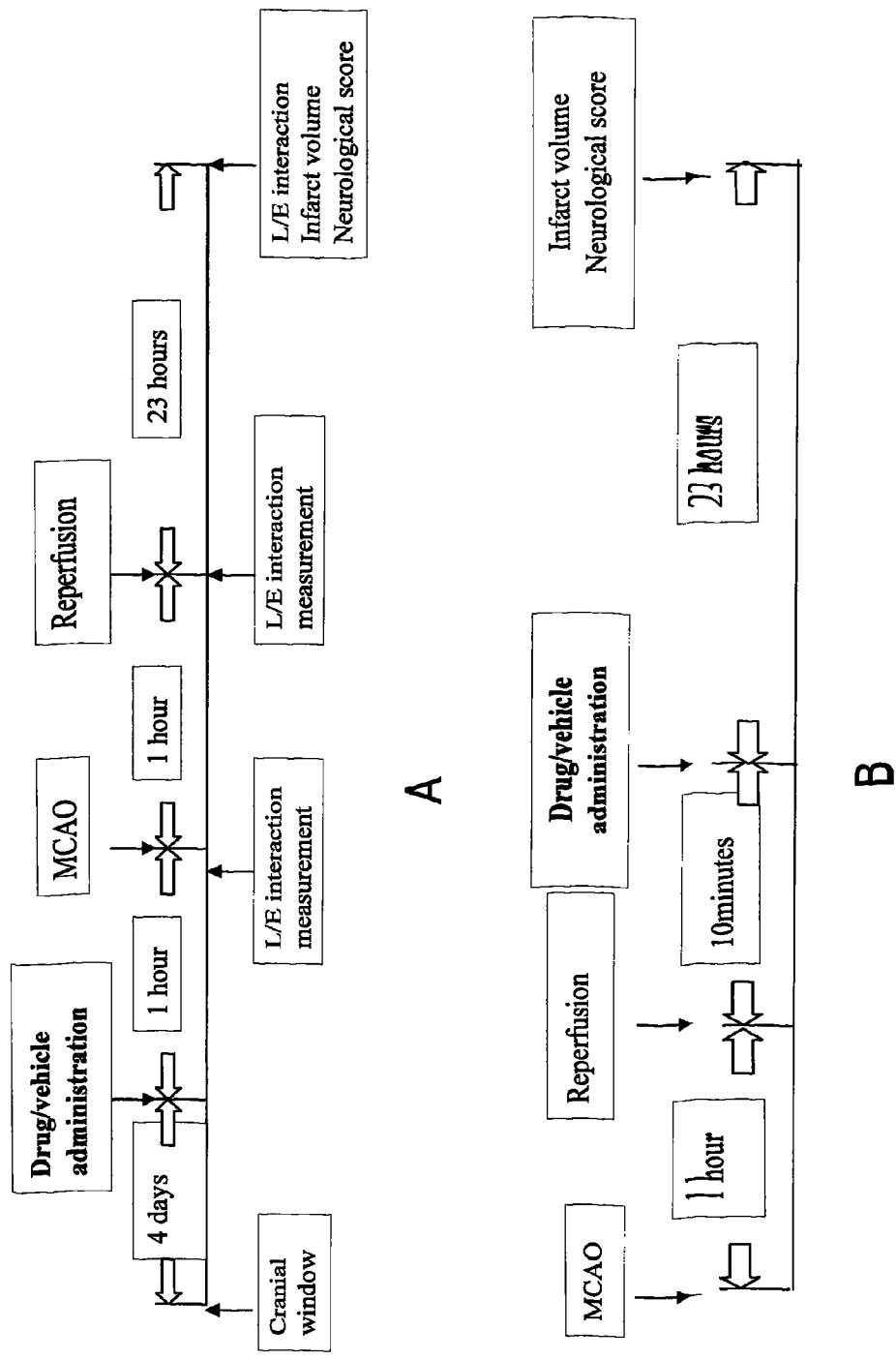

Crocker et al., "Development of Agonists, Partial Agonists and Antagonists in the $\Delta^8$-Tetrahydrocannabinol Series," *Tetrahedron*, 55: 13907-13926, 1999.
Devane et al., "Isolation and Structure of a Brain Constituent that Binds to the Cannabinoid Receptor," *Science*, 258: 1946-1949, 1992.
Devane et al., "Determination and Characterization of a Cannabinoid Receptor in Rat Brain," *Molecular Pharmacology*, 34: 605-613, 1988.
Drake et al., "Classical/Nonclassical Hybrid Cannabinoids: Southern Aliphatic Chain-Functionalized C-6β Metyl, Ethyl, and Propyl Analogues," *J. Med. Chem.*, 41: 3596-3608, 1998.
Gareau et al., "Structure Activity Relationships of Tetrahydrocannabinol Analogues on Human Cannabinoid Receptors," *Bioorg. Med. Chem.*, 6(2): 189-194, 1996.
Hanus et al., "HU-308: A Specific Agonist for $CB_2$, a Peripheral Cannabinoid Receptor," *Proc. Natl. Acad. Sci. USA*, 96(25): 14228-14233, 1999.
Huffman et al., "A Pyridone Analogue of Traditional Cannabinoids. A New Class of Selective Ligands for the $CB_2$ Receptor," *Bioorg. Med. Chem.*, 9: 2863-2870, 2001.
Huffmann, et al., "3-(1',1'-Dimethylbuyl)-1-deoxy-$\Delta^8$-THC and Related Compounds: Synthesis of Selective Ligands for the $CB_2$ Receptor," *Bioorg. Med. Chem.*, 7: 2905-2914, 1999.
Little et al., "Pharmacology and Stereoselectivity of Structurally Novel Cannabinoids in Mice," *J. Pharmacol. Exp. Ther.*, 247(3): 1046-1051, 1988.
Mahadevan et al., "Novel Cannabinol Probes for CB1 and CB2 Cannabinoid Receptors," *J. Med. Chem.*, 43: 3778-3785, 2000.
Munro et al., "Molecular Characterization of a Peripheral Receptor for Cannabinoids," *Nature*, 365: 61-65, 1993.
Reggio et al., "Importance of the C-1 Substituent in Classical Cannabinoids to $CB_2$ Receptor Selectivity: Synthesis and Characterization of a Series of O,2-Propano-$\Delta^8$-Tetrahydrocannabinol Analogs," *J. Med. Chem.*, 40: 3312-3318, 1997.
Rinaldi-Carmona et al., "SR 141716A, a Potent and Selective Antagonist of the Brain Cannabinoid Receptor," *FEBS Letters*, 350: 240-244, 1994.
Ross et al., "Agonist-inverse Agonist Characterization at $CB_1$ and $CB_2$ Cannabinoid Receptors of L759633, L759656 and AM630," *British J. Pharmacology*, 126: 665-672, 1999.
Ryan et al., "Potent Anandamide Analogs: The Effect of Changing the Length and Branching of the End Pentyl Chain," *J. Med. Chem.*, 40: 3617-3625, 1997.
Seltzman et al., "Synthesis and Pharmacological Comparison of Dimethylheptyl and Pentyl Analogs of Anandamide," *J. Med. Chem.*, 40: 3626-3634, 1997.
Sheskin et al., "Structural Requirements for Binding of Anandamide-Type Compounds to the Brain Cannabinoid Receptor," *J. Med. Chem.*, 40: 659-667, 1997.
Showalter et al., "Evaluation of Binding in a Transfected Cell Line Expressing a Peripheral Cannabinoid Receptor (CB2): Identification of Cannabinoid Receptor Subtype Selective Ligands," *J. Pharmacol. Exp. Ther.* 278(3): 989-999, 1996.
Song et al., "A Lysine Residue of the Cannabinoid Receptor is Critical for Receptor Recognition by Several Agonists but not WIN5521-2," *Mol. Pharmacol.*, 49: 891-896, 1996.
Thomas et al., "Structure-Activity Analysis of Anandamide Analogs: Relationship to a Cannabinoid Pharmacophore," *J. Med. Chem.*, 39: 471-479, 1996.
Wiley et al., "Structure-Activity Relationships of Indole- and Pyrrole-Derived Cannabinoids," *J. Pharmacol. Exp. Ther.*, 285(3): 995-1004.
Farooqui, A.A. et al. "Modulation of inflammation in brain: a matter of fat," J. Neurochemistry, 2007, 101: 577-599.
Huffman, J.W. et al. "Synthesis and Pharmacology of a Very Potent Cannabinoid Lacking a Phenolic Hydroxyl with High Affinity for the CB2 Receptor," J. Med. Chem., 1996, 39: 3875-3877.
Schmidt-Glenewinkel, T. et al. "Chapter 7: Inflammation as a Mediator of Oxidative Stress and Ups Dysfunction," in *The Proteasome in Neurodegeneration*, Ed. Stefanis and Keller, 2006, Springer: New York, NY, pp. 105-131.
Amantea et al. (*FEBS J.* 274:4464-4775 (2007).
Cabral and Marciano-Cabral, *Journal of Leukocyte Biology* 78:1192-1197 (2005).
Engelhardt and Ransohoff, *TRENDS in Immunology*, 26:485-495 (2005).
Gelderblom et al., *Journal of the American Heart Association*, 40:1849-1857 (2009).
Graeber et al., *FEBS Letters*, 585:3798-3805 (2011).
Hillard, *Curr. Pharm. Des.* 14:2347-2361 (2008).
Iadecola and Anrather, *Nature Medicine* 17:796-808 (2011).
Jin et al., *Ann. Neurol.* 48:257-261 (2000).
Liu et al., *Life Sciences* 89:141-146 (2011).
Muthian et al., *Neuroscience* 129:743-750 (2004).
Nagayama et al., *J. Neurosci.* 19(8):2987-95 (1999).
Parmentier-Batteur et al., *J. Neurosci.* 22(22):9771-5 (2002).
Persidsky et al., *J. Neuroimmune Pharmacol.* 1: 223-236 (2006).
Saunders et al., *Clin Exp Pharmacol Physiol*. 26:11-19 (1999).
Sommer et al., *Acta Neuropathol.* 112: 277-286 (2006).
Ulrich et al., *Journal of Neuroimmunology*, 184:127-135 (2007).
Adhikary et al., Journal of Neurotrauma, 28:2417-27 (2011).

\* cited by examiner

INFLAMMATION THERAPY

This application claims the benefit of U.S. Provisional Application No. 60/872,794, filed Dec. 5, 2006.

The present invention relates to methods of treating diseases and disorders of the central nervous system (CNS) by administration of Cannabinoid $CB_2$ receptor agonists. Particularly treated are inflammatory components within the CNS, such as occur with head and spinal trauma, stroke, cerebral bleeds, reperfusion injury, Alzheimer's and Parkinson's diseases and CNS features of multiple sclerosis, eg. Primary and Secondary progressive MS.

*Cannabis*, the natural marijuana plant, has been used for its psychotropic and possible medical properties for thousands of years. Cannabinoids, the synthetic analogs of *cannabis*, have been found recently to have different neuromodulatory properties in both in vivo and in vitro studies (Klein et al. 2001). So far, there are two cloned cannabinoid receptors, designated $CB_1$ and $CB_2$. The $CB_1$ receptor is expressed in the central nervous system (CNS), exhibiting a presynaptic location and playing a prominent role in synaptic neurotransmission. Because of the involvement of the $CB_1$ receptor in modulating synaptic transmission, and therefore the potential to attenuate excitotoxic injury following ischemia, the $CB_1$ receptor has been a target for the modulation of injury following ischemia (Muthian et al. 2004; Nagayama et al. 1999; Parmentier-Batteur et al. 2002).

The $CB_2$ receptor is expressed predominantly by cells of the immune system, such as lymphocytes and neutrophils, but is also expressed on resident inflammatory cells within the CNS (Klein et al. 2001; Maresz et al. 2005; Pertwee 1999). $CB_2$ stimulation has been shown to have immunomodulatory properties, such as decreasing antigen presenting cell (APC) activity and down-regulation of cytokines (IFN-$\gamma$ and TNF-$\alpha$) production during an inflammatory response. Recently the $CB_2$ receptor has been identified on microglials and dendritic cells, implying a complicated role in CNS inflammatory response (Croxford 2003; Pertwee 1999). A number of investigations have shown that $CB_2$ receptor activation has anti-inflammatory therapeutic potential in CNS diseases, such as multiple sclerosis, traumatic brain injury and Alzheimer's disease (Grundy et al. 2001; Jackson et al. 2005; Ni et al. 2004).

Previous studies have investigated the potential neuroprotective properties of cannabinoids following ischemia. However these studies have focused on activation of the $CB_1$ receptor rather than activation of the $CB_2$ receptor. Both $CB_1$ and $CB_2$ receptors are found in the brain. $CB_1$ is predominately expressed in CNS and peripheral neurons and $CB_1$ stimulation is important in neurotransmission and CNS homeostasis (Grundy 2002; Pertwee 1999; Rodriguez de Fonseca et al. 2005). The ability of the $CB_1$ receptor which is thought to inhibit presynaptic transmission has been postulated to protect neurons from excitotoxic injury following ischemia.

Consistent with this hypothesis, the $CB_1/CB_2$ agonist tetrahydrocannabinol was shown to reduce cerebral infarction in a mouse model of MCAO by $CB_1$ receptor via inducing hypothermia (Hayakawa et al. 2004). Cannabidiol, the nonpsychoactive constituent of *cannabis*, also reduced cerebral infarction but this is thought to be due to increasing rCBF during ischemia via the serotonergic 5-hydroxytryptamine$_{1A}$ receptor (Mishima et al. 2005). WIN55212-2, which stimulates both the $CB_1$ and $CB_2$ receptor, with greater affinity for the $CB_2$ receptor, has been demonstrated to be neuroprotective in both global and focal models of ischemia.

Based upon the use of WIN55212-2 in combination with a $CB_1$ antagonist, these effects were interpreted to be the result of $CB_1$ receptor activation (Nagayama et al. 1999). Moreover, an investigation utilizing $CB_1$ knockout mice demonstrated an increase in infarct size compared to wild type animals (Parmentier-Batteur et al. 2002). However in a separate investigation utilizing the $CB_1$ receptor antagonist SR141716 blockade of this receptor was found to reduce infarct volume in a mouse Mid Carotid Artery Occulsion—MCAO—model (Muthian et al. 2004). Because of the conflicting nature of these results the potential of the $CB_1$ receptor as a therapeutic target for neuroprotection following ischemia/reperfusion injury remains an open question.

The hypothesis investigated in the current study was that activation of the $CB_2$ receptor might provide protection from cerebral ischemia/reperfusion injury through a completely separate mechanism. This hypothesis was based upon a number of studies that have demonstrated a modulation of inflammation by $CB_2$ agonists in models of multiple sclerosis, traumatic brain injury and Alzheimers disease (Jackson et al. 2005; Ni et al. 2004; Schwenkreis and Tegenthoff 2003; Walter and Stella 2004). $CB_2$ is mainly located on immune cells and its stimulation has been show to modulate immune cells activities and inflammatory responses.

$CB_2$ is a $G_i$ protein coupled-receptor and its activation triggers a series of signal transduction pathways which eventually leads to either up- or down-regulation of gene transcription. In most cases, the genes involved are coded for pro-inflammatory cytokines (Klein et al. 2001). Inhibition of cytokines such as TNF-$\alpha$ and IL-6 by $CB_2$ activation had been demonstrated in both in vivo and in vitro studies. In addition, iNOS transcription and NO production in macrophage can be largely inhibited by $CB_2$ activation (Berdyshev 2000). Both pro-inflammatory cytokines and NO are neurotoxic, leading to neuronal death during stroke.

$CB_2$ stimulation is also able to inhibit antigen presenting cell (APC) activity, decrease antibody production from B lymphocytes and down-regulate inflammatory cytokine production (Klein and Gabral 2006). All of these investigations indicate that activation of the $CB_2$ receptor may provide a potent mechanism for interference with inflammatory response.

Inflammation has been shown to be an important contributor to damage to the brain following ischemia/reperfusion injury (Danton and Dietrich 2003; Iadecola and Alexander 2001). The contribution of white blood cell invasion from the circulating blood to this process has been demonstrated in early studies that relied upon depletion of white blood cells, and later studies that utilized adhesion molecule blockers (Connolly et al. 1996; Sughrue et al. 2004). Within minutes of ischemia, cerebral vascular endothelium is activated and leukocytes begin to roll on inflamed endothelial cells.

Once activated, leukocytes begin to firmly adhere to endothelial cells. This process is mediated by a series of interactions between cell adhesion molecules (CAMs) expressed on both leukocytes and endothelial cells. CAMs, such as ICAM-1, can be highly induced during an early stage of ischemia by pro-inflammatory cytokines such as TNF-$\alpha$ (Kataoka et al. 2004; Kishimoto and Rothlein 1994). Following cerebral ischemia, neutrophils are the first leukocytes to infiltrate the site of inflammation and monocytes are subsequently recruited. Leukocytes activation and migration have been implicated as primary contributors to ischemia/reperfusion injury. In addition to their role in physical obstruction of capillaries, they participate in inflammatory responses and cause brain tissue damage by various mechanisms. Pro-inflammatory cytokines (TNF-α and IL-1β) secreted by leukocytes not only activate vascular endothelial cells and amplify inflammatory response but also directly induce neuronal injury (Wood 2003).

Matrix metalloproteases (MMPs), secreted by macrophages, can degrade constituents of basal lamina thus contribute to blood-brain-barrier disruption and cerebral edema during stroke (Maier et al. 2004). All of these studies highlight the involvement of white blood cells in exacerbating ischemic injury, and the protection offered by interfering with the ability of white blood cells to adhere to endothelial cells and undergo diapedesis into the brain (Heinel et al. 1994; Vasthare et al. 1990; Weaver et al. 2002; White et al. 2000).

Since inflammatory responses following ischemia have been shown to be important contributors to secondary injury, the present inventors hypothesized that selective activation of the $CB_2$ receptor might provide protection from reperfusion injury. Although cannabinoids have been tested in models of cerebral ischemia/reperfusion injury and reported to influence stroke outcomes by a variety of mechanisms, none of these studies has focused on the possible role of the $CB_2$ receptor in modulating the inflammatory response during cerebral ischemic and reperfusion injury.

The present inventors are thus believed to be the first to identify the role of selective $CB_2$ receptor activation in attenuating ischemia/reperfusion injury. They have determined that $CB_2$ cannabinoid receptor agonists provide the significant protection for the brain from cerebral ischemia/reperfusion injury in mouse Mid Carotid Artery Occlusion/Reperfusion model. Animals treated with the $CB_2$ agonists had smaller infarct volumes and improved motor function 24 hours following the ischemic episode.

Using $CB_2$ agonists O-3853 and O-1966, which both have excellent affinity for $CB_2$ receptors and very low affinity for $CB_1$ receptors, the inventors have demonstrated that activation of the $CB_2$ receptor is neuroprotective following ischemia/reperfusion injury. These analogs were also effective in activating the $CB_2$ receptor, but not $CB_1$ receptors, as evidenced by their effects on $^{35}S$-GTPγS binding. Consistent with their binding profiles, O-3853 failed to produce $CB_1$ receptor-mediated behavioral effects in mice even up to very high doses and O-1966 produced some modest behavioural effects only at doses that far exceeded those used in the MCAO/R studies.

In a first aspect of the present invention there is provided a method of treating a patient in need of therapy for a central nervous system inflammatory disorder comprising administering to that patient a therapeutically effective amount of a cannabinoid agonist having a binding affinity ratio at cannabinoid receptors, Ki $CB_1$/Ki $CB_2$, of at least 5, still more preferably at least 50 and still more preferably at least 500. Most preferred agonists have a binding affinity ratio of 5000 or more when they have $CB_1$ agonist activity, but this may be lower where it is a $CB_1$ partial agonist or antagonist. The Ki ratios may be measured with respect to rat receptor binding. Preferably these ratio requirements are also met in respect to human receptors.

Preferably the agonist has at least 60% maximal activity at the human $CB_2$ receptor as measured in the $^{35}S$-GTPγS assay. More preferably the agonist has at least 80% efficacy and even more preferably at least 95%. Efficacy is as a percentage of maximal effect is measured using the model $CB_1$/$CB_2$ agonist CP55,940 in cells expressing h$CB_2$ receptors. It will be realised that the most preferred $CB_2$ agonists will be more efficacious than CP55,940 and thus will have efficacy of 110% or more.

Preferably the agonist is a partial agonist at the $CB_1$ receptor, having less than 100% efficacy at its maximally effective dose, more preferably less than 80% efficacy and most preferably less than 60% efficacy, efficacy being as a percentage of maximal effect using the model $CB_1$/$CB_2$ receptor agonist WIN55212-2 in rat brain membranes.

Preferably the agonist has a Ki (75 nM) at the rat $CB_2$ receptor of at most 150 nM, more preferably at most 75 nM and still more preferably less than 30 nM, most preferably less than 20 nM. Particularly illustrated compounds are resorcinols and these have Ki (nM) at the rat $CB_2$ receptor of from 2 to 30 nM.

Examples of available $CB_2$ agonists from the prior art are AM1241

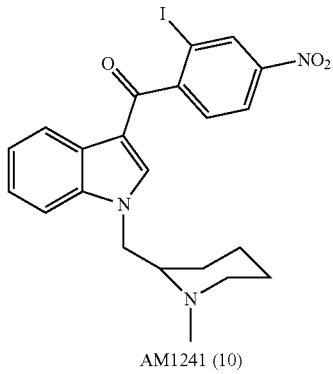

AM1241 (10)

JWH-133,

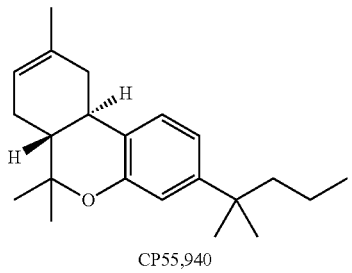

CP55,940

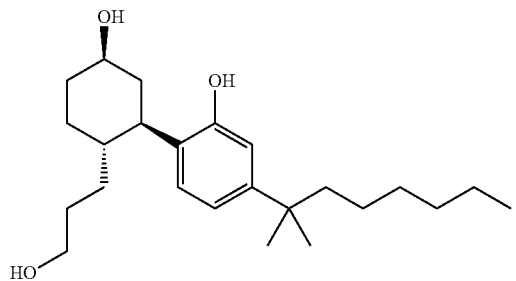

CP-55,940 (2)

and PRS 211,375 (Cannabinor).

-continued

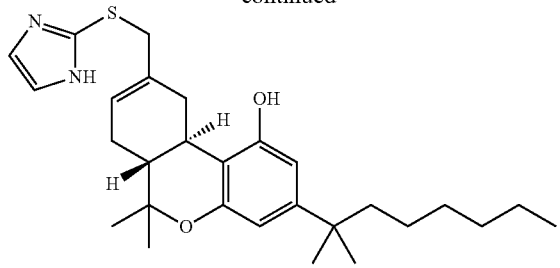

WIN55,212-2 is of formula

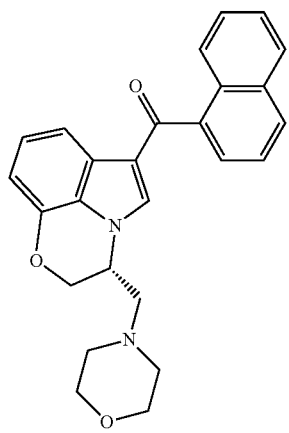

Further examples of CB$_2$ agonists are described in Gertsch et al; Journal of Receptors and Signal Transduction, 26:709-730, 2006, incorporated herein by reference.

Preferred agonists are resorcinols disclosed by Wiley et al, incorporated herein by reference, such as O-1966. Further preferred compounds are 3, 5 dihydroxyphenyl analogues of such resorcinols as described in the presently copending US provisional application 'Cannabinoids (II))' of Razdan et al, eg. O-3853, filed Dec. 5, 2006 incorporated herein by reference.

O-1966 has formula

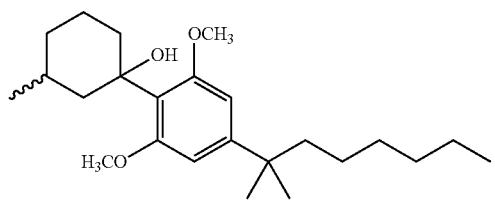

In a further embodiment the present invention provides a method of the first aspect where a CB$_2$ agonist is administered in combination with a CB$_1$ antagonist. Such a method would particularly be effective prophylactically.

The present invention will now be described further by reference to the following non-limiting examples, tables and figures. Further embodiments falling within the scope of the claims will occur to those skilled in the art in the light of these.

FIGURES

FIG. 1. Experimental designs for pre-ischemic treatment test (A) and post-reperfusion treatment test (B).

Figure 2:
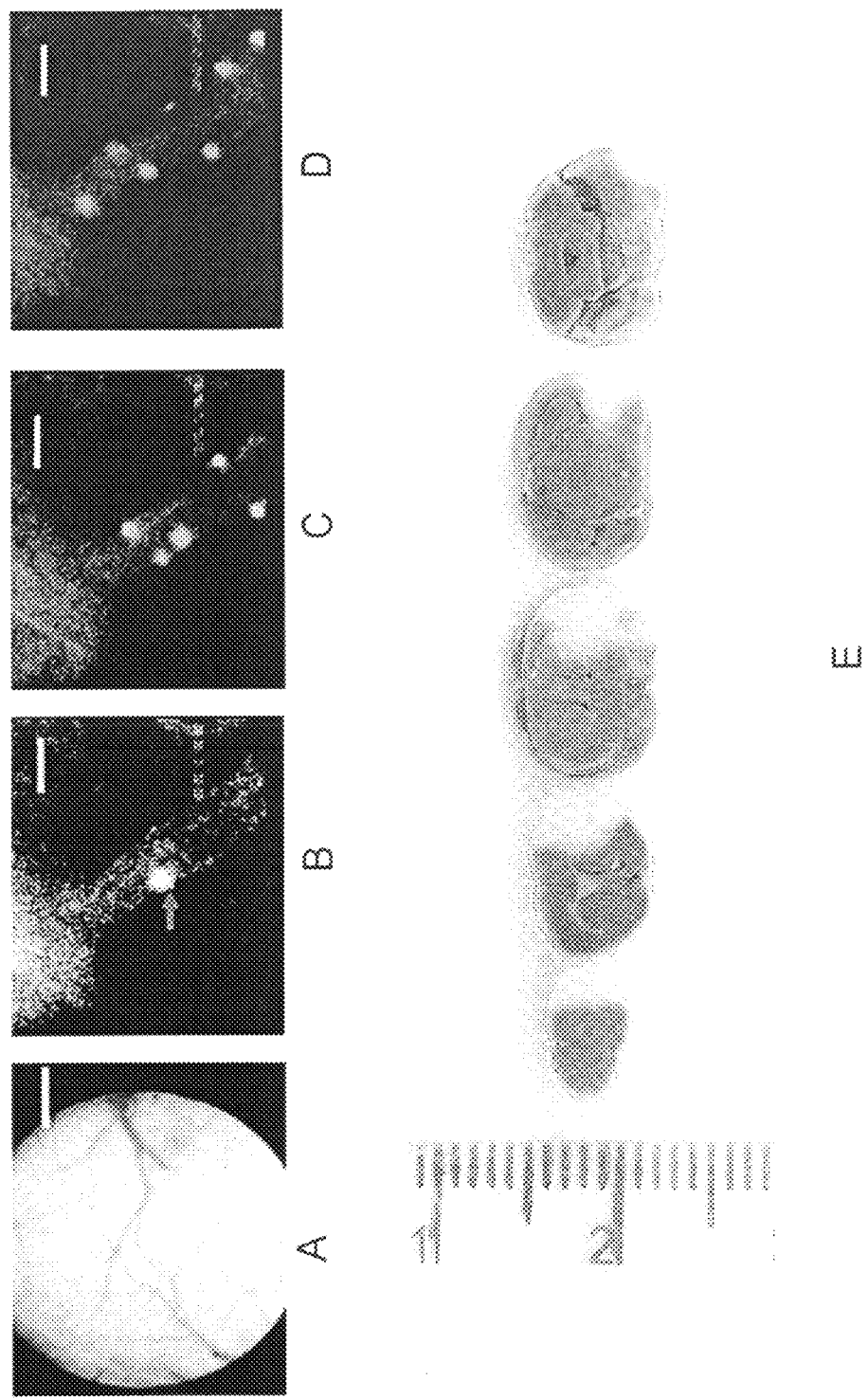

FIG. 2. Typical closed cranial window video images (A)-(D) and infarct areas (E) of MCAO mouse.

Figure 3:
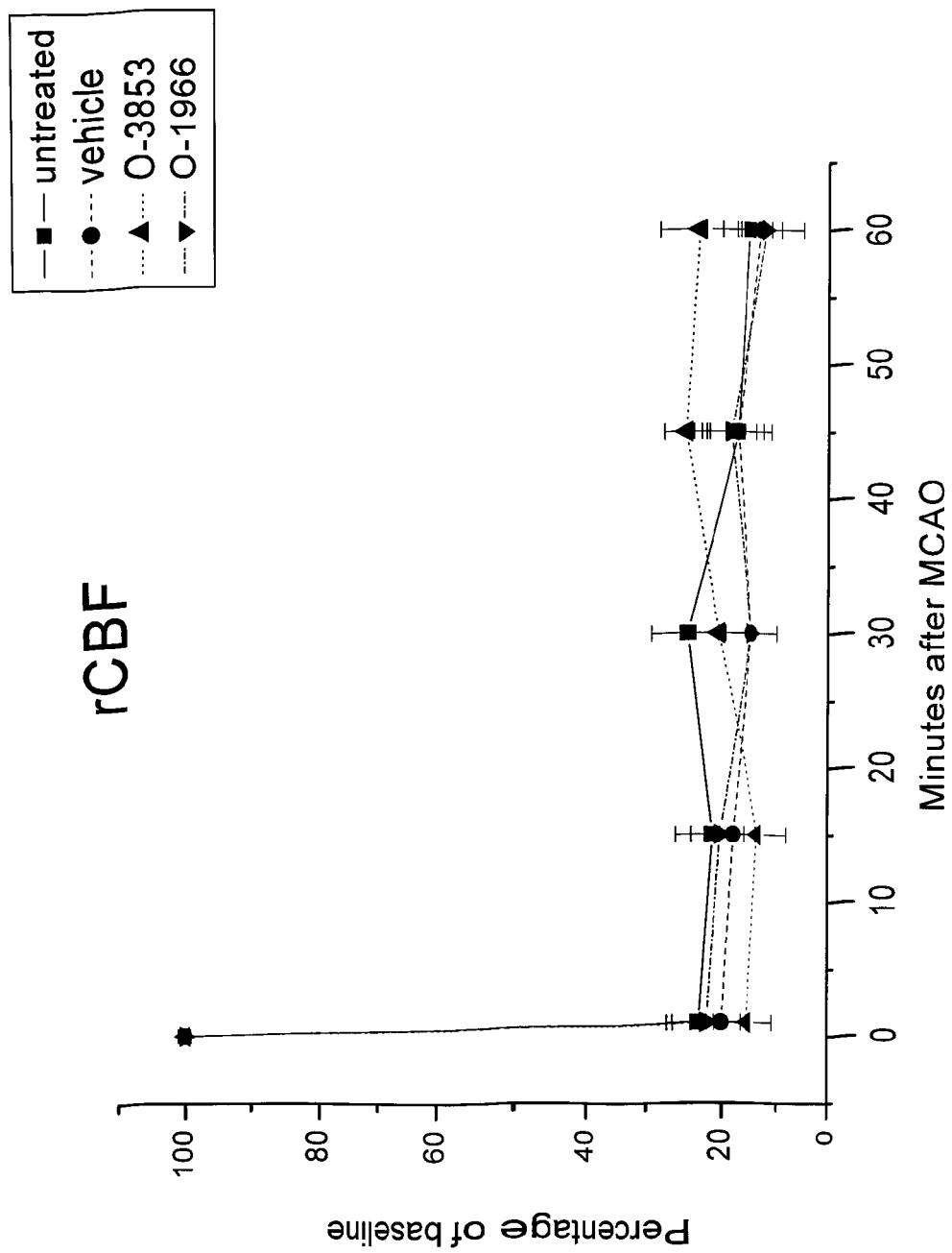

FIG. 3. Graph of rCBF with time for CB$_2$ agonists (O-3853 or O-1966) compared with vehicle treated control group.

Figure 4:
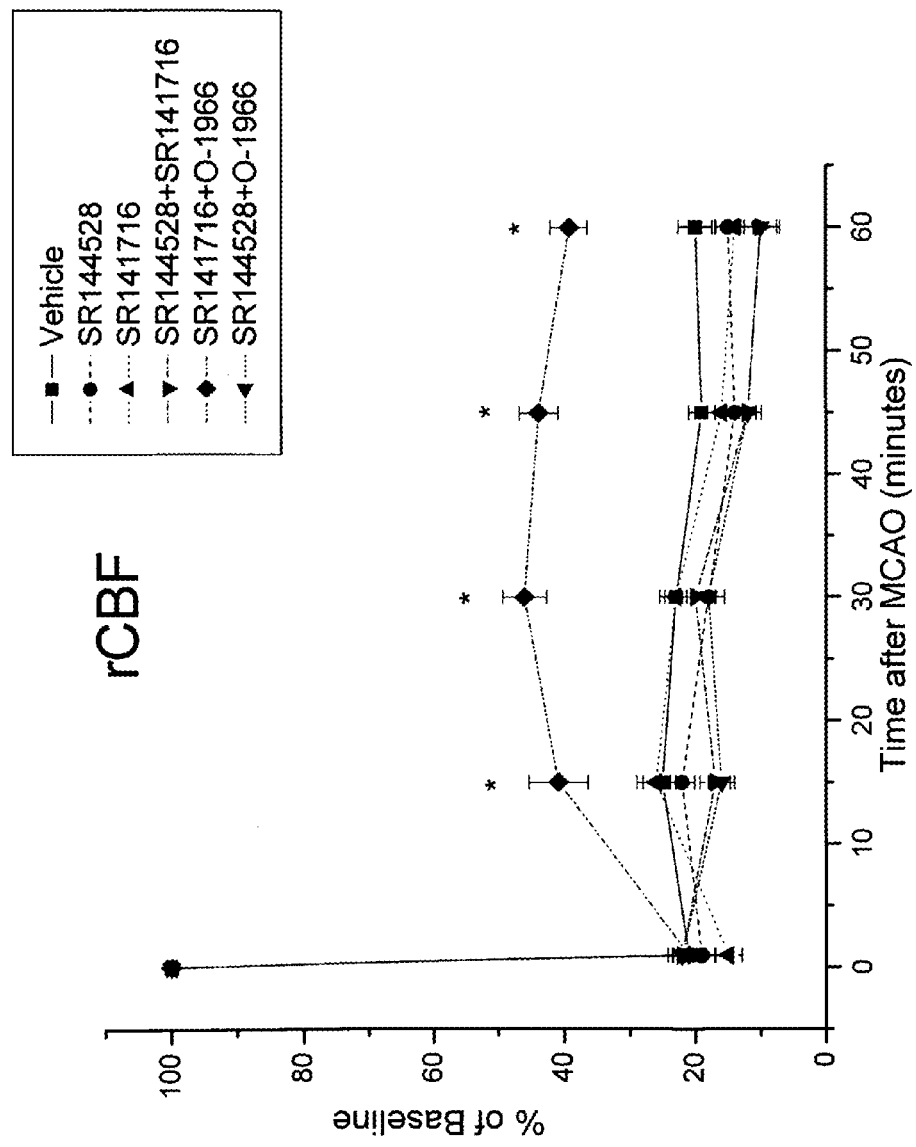

FIG. 4. Graph of rCBF with time for model CB$_1$ and CB$_2$ antagonists alone, together and with O-1966.

Figure 5:
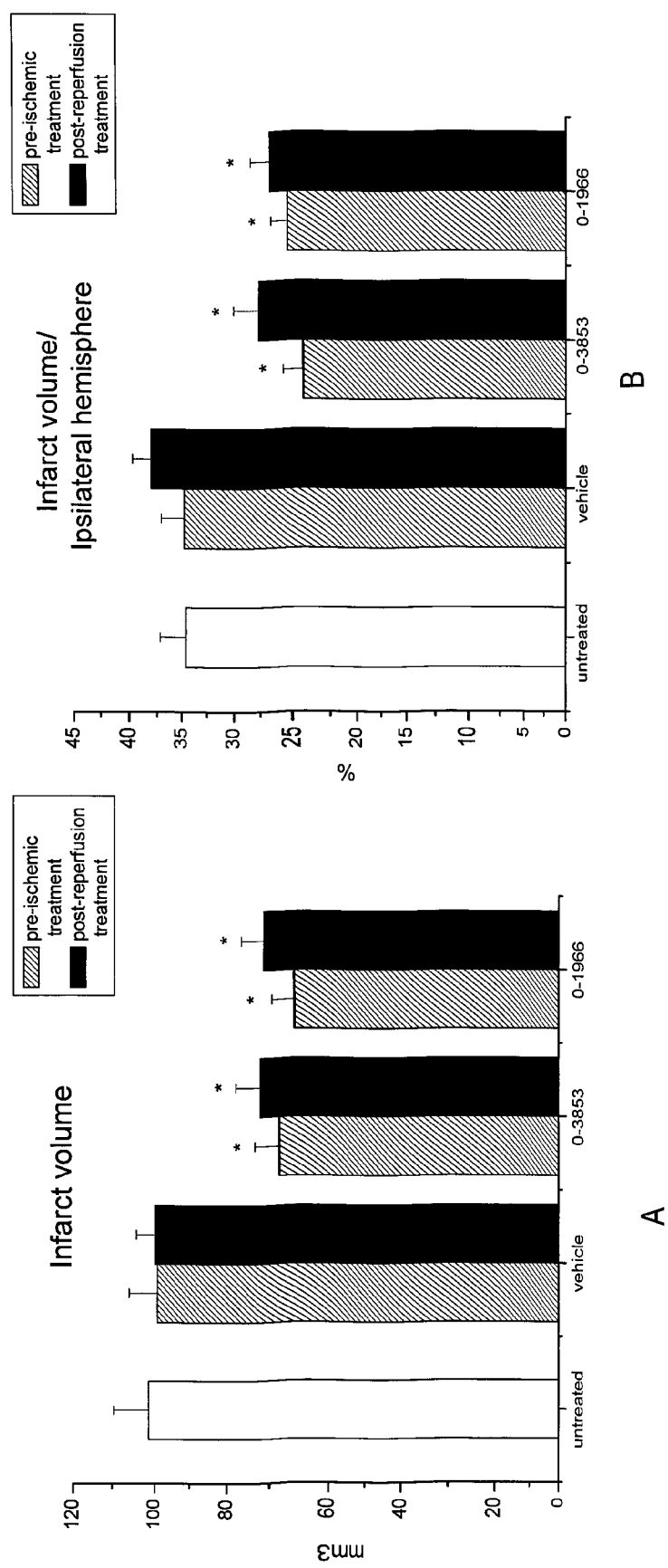

FIG. 5. Histograms of infarct vol mm3 and % of the ipsilateral hemisphere with time with and without CB$_2$ agonists (O-3853 or O-1966) for either 1 hour before MCAO or 10 minutes after reperfusion significantly.

Figure 6:
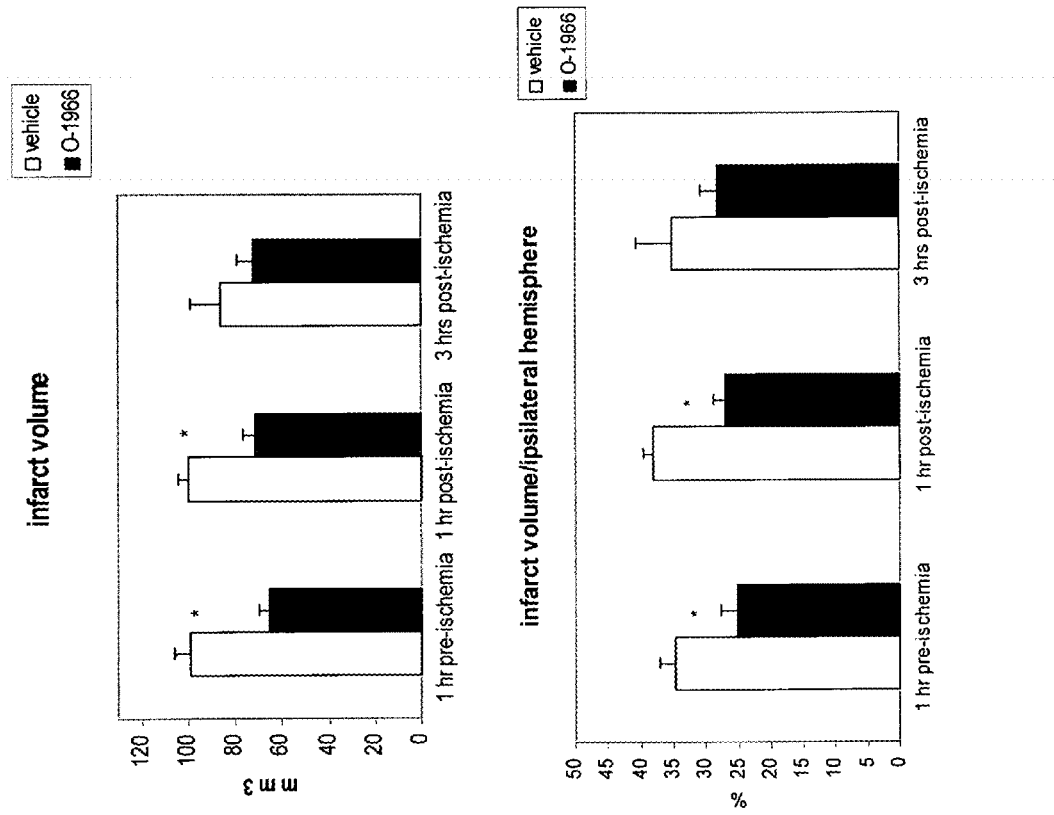
Figure 7:
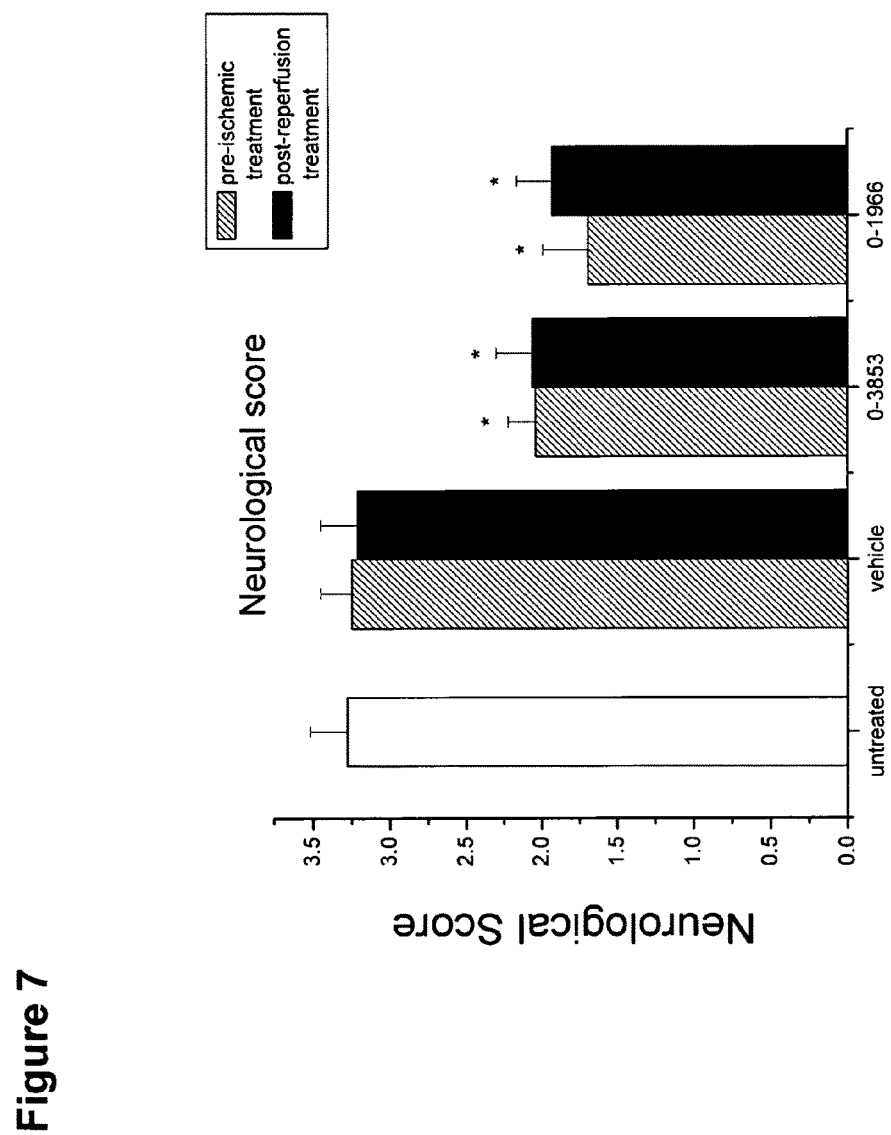

FIG. 6. Histogram of infarct volume in mm3 and % ipsiteal hemisphere with and without O-1966 treatment at 1 hr pre, 1 hr post and 3 hours post ischemia FIG. 7. Histogram of Neurological score at 23 hours after insult with and without CB$_2$ agonists (O-3853 or O-1966) 1 hour before MCAO and 10 minutes after reperfusion.

Figure 8:
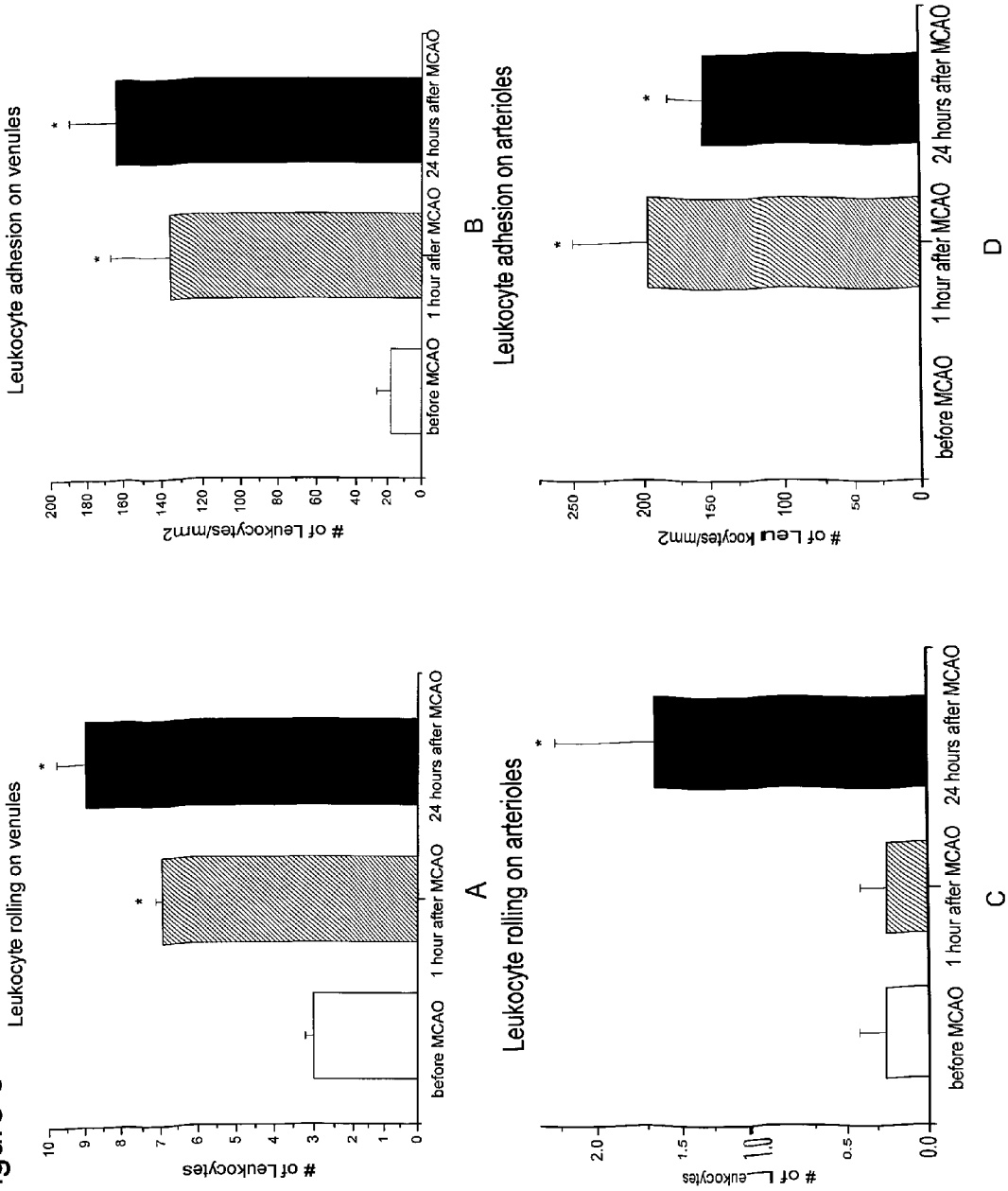

FIG. 8. Histograms of leukocyte rolling after MCAO and adhesion following reperfusion with and without CB$_2$ agonists (O-3853 or O-1966).

Figure 9:
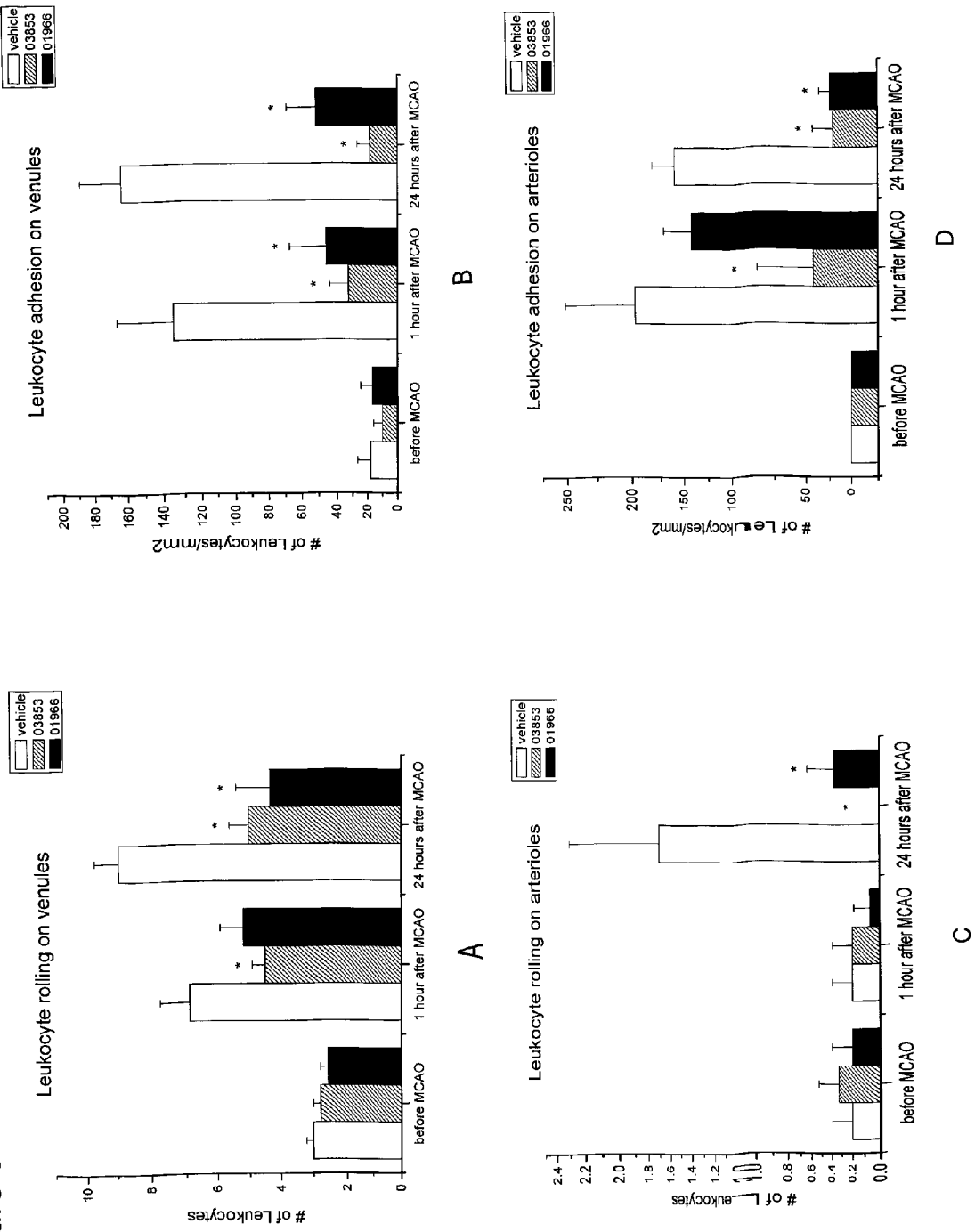

FIG. 9. Histograms of Leukocyte rolling after administration of either CB$_2$ agonist (O-3853 or O-1966) either 1 hour before MCAO attenuated leukocyte/endothelial interactions.

Figure 10:
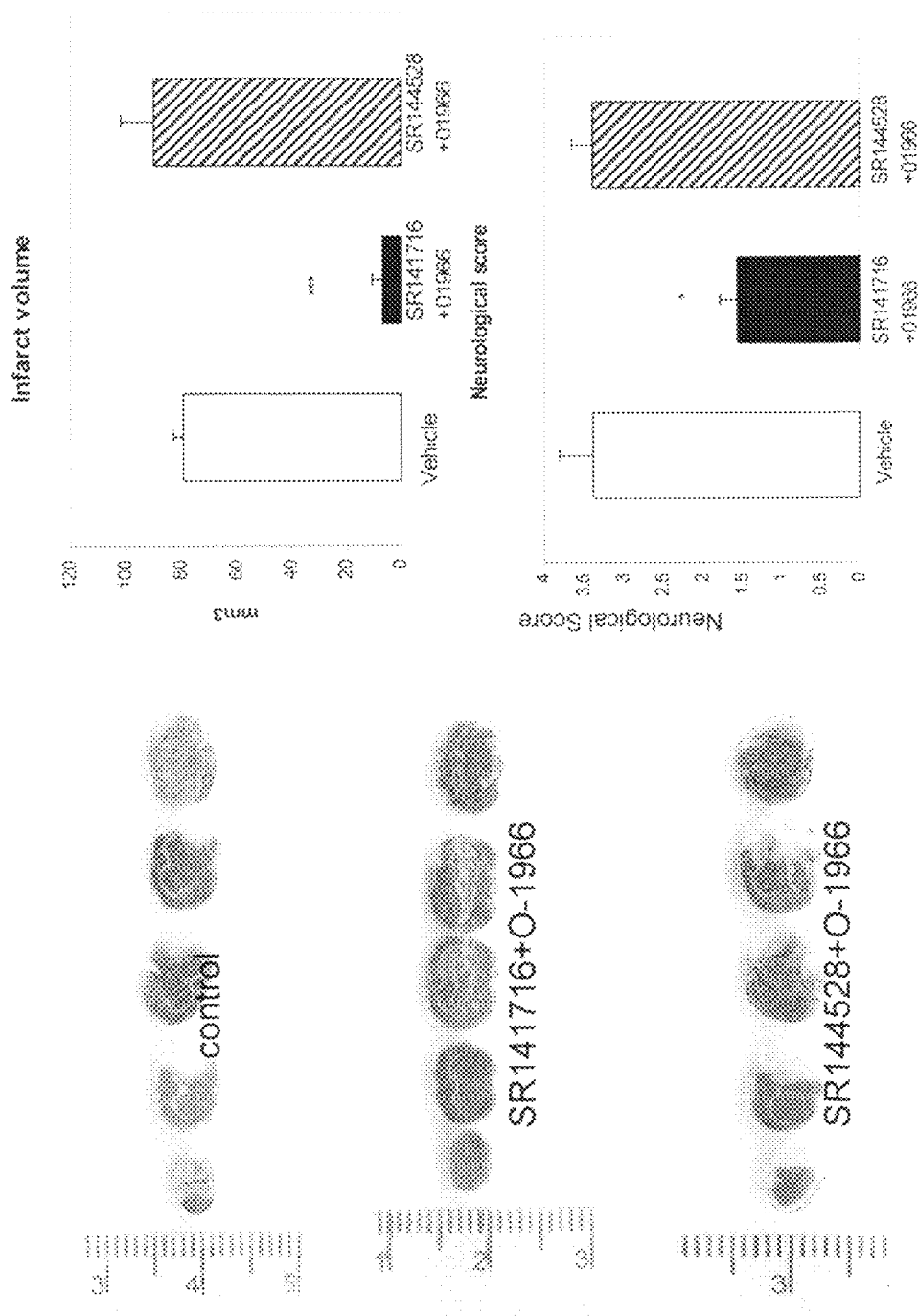

FIG. 10. Infarct areas and histograms for effect of SR141716 and SR144528 administered 1 hour before MCAO at 20 mg/kg i.p. O-1966 was injected 1 hour before MCAO at 1 mg/kg i.v. n=5-7 per group.

Figure 11:
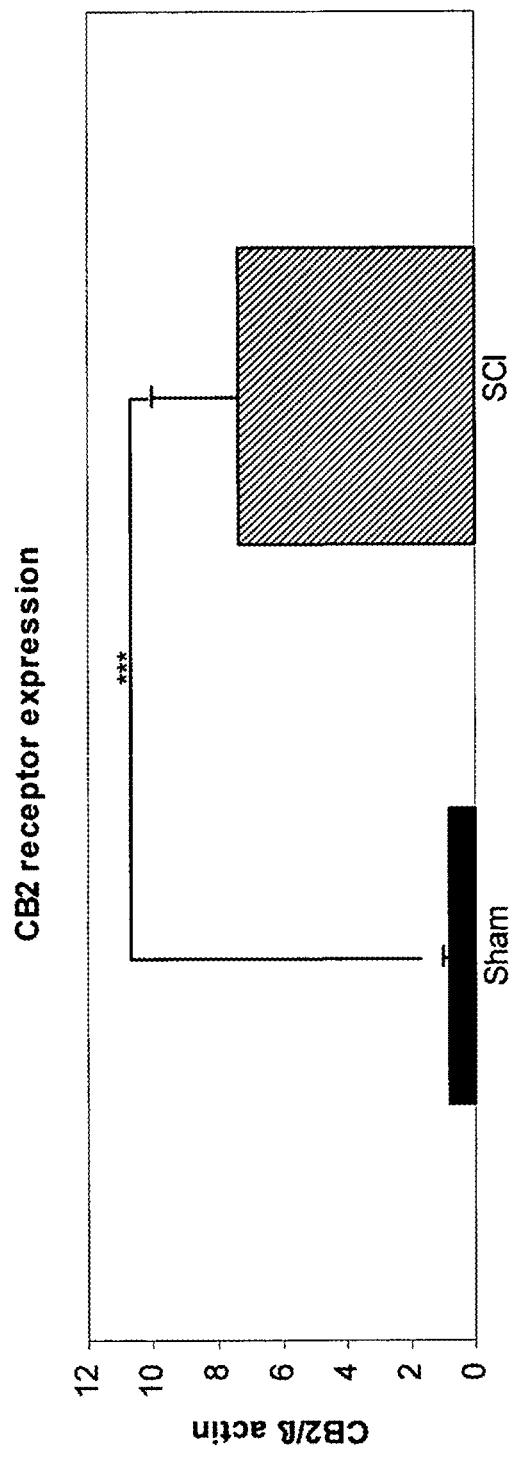

FIG. 11. Histogram of CB$_2$ mRNA expression for sham and spinal cord injury (SCI) contusion model mice.

Figure 12:
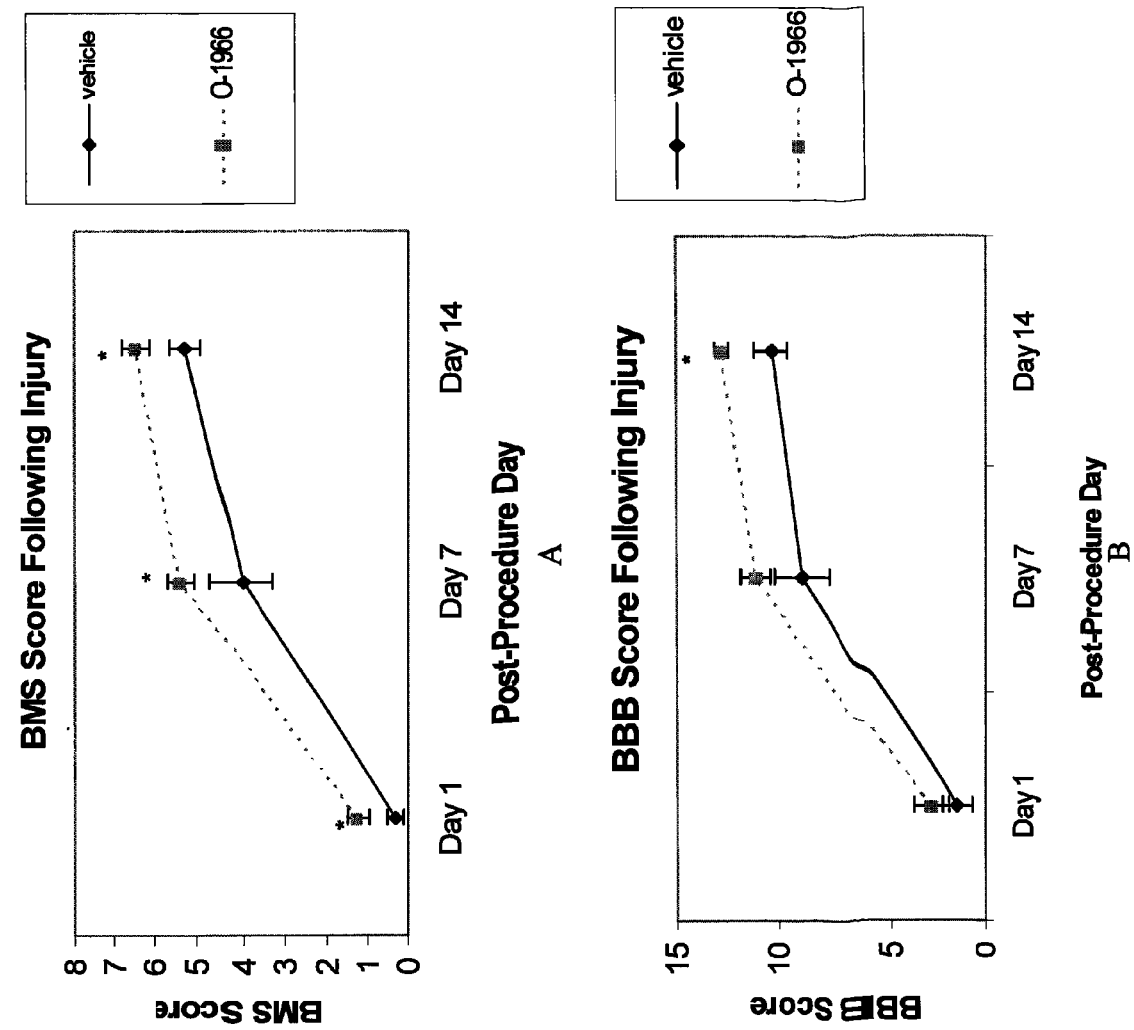

FIG. 12. Plots of BMS and BBB score with time following SCI with vehicle and CB$_2$ agonist O-1966.

Figure 13:
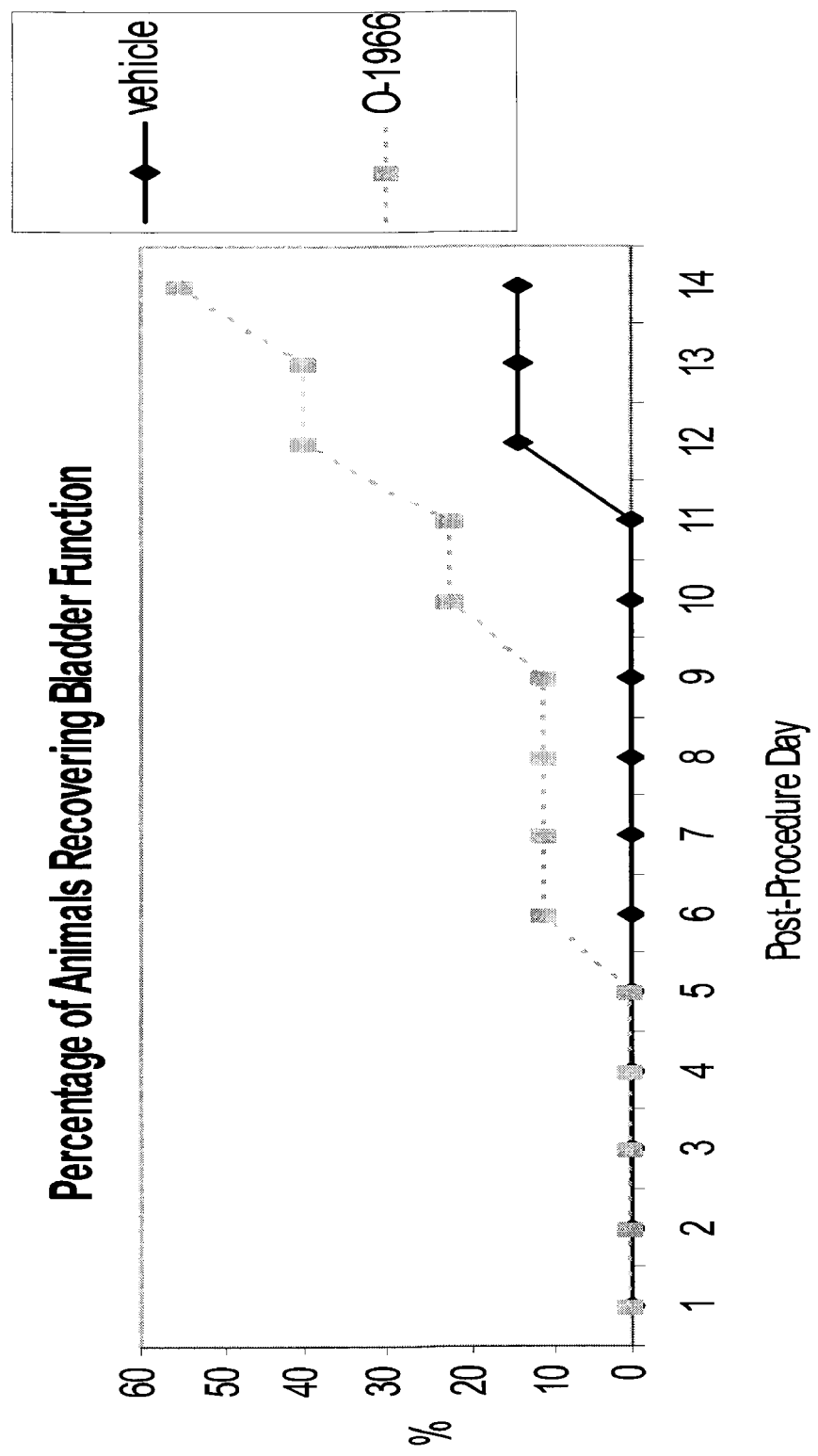

FIG. 13. Plots of % animals recovering bladder function with time after SCI with vehicle and with O-1966.

Figure 14:
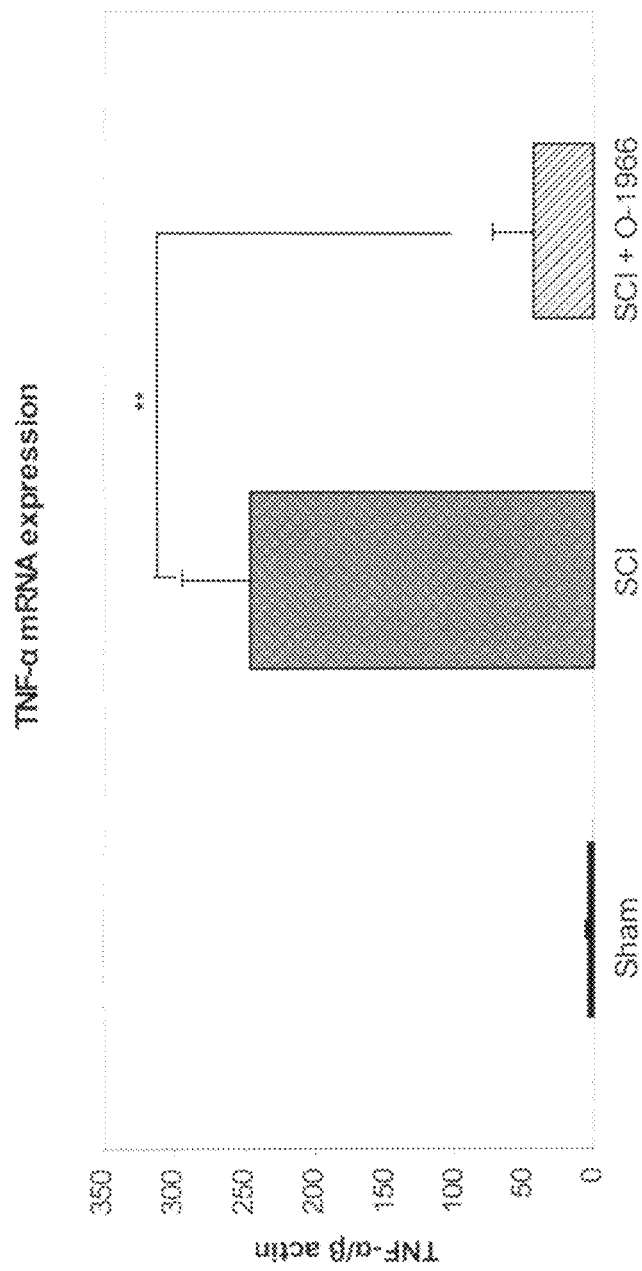

FIG. 14. Histogram of TNF-α expression in sham, SCI and SCI with O-1966.

EXAMPLES

Materials and Methods
Animals

The cerebral ischemia/reperfusion studies were carried out on 8 week old male C57BL/6 mice (weighing 23 to 27 g; Taconic N.Y.) and conducted in accordance with the guidelines approved by Institute for Animal Care and Use Committee at Temple University. The behavioural evaluation of the cannabinoid analogs was carried out in 8-week old ICR male mice weighing 23-27 g in accordance with the guidelines approved by the Institute for Animal Care and Use Committee at Virginia Commonwealth University.

In Vitro and In Vivo Evaluation of CB$_2$ Receptor Selectivity

Both analogs depicted below were assessed for cannabinoid properties by determining their affinities for CB$_1$ and CB$_2$ receptors, functional activity using $^{35}$S-GTPγS binding, and assessment in cannabinoid behavioural assays in mice using methodologies described in detail in recent publications. (Martin et al. 2002; Wiley et al. 2002) CB$_1$ and CB$_2$ receptor affinities were determined using $^3$H-CP 55,940 binding to rat brain membranes and to Chinese Hamster Ovary (CHO) cells stably expressing the human CB$_2$ receptor, respectively. In vitro functional activity was determined in these same preparations using $^{35}$S-GTPγS binding. For in vivo behavioural effects, mice were injected intravenously with the drugs prepared in ethanol:emulphor:saline (1:1:18). The mice were evaluated for locomotor activity, analgesia, body temperature, and catalepsy. These behaviours are collectively referred to as the tetrad test and are indicative of $CB_1$ receptor activity.

Cranial Windows

On the day of cranial window implantation, the animals were anesthetized with an intraperitoneal injection of Ketamine (100 mg/ml)-Xylazine (20 mg/kg) mixture (1:1) at a dose of 1 ml/kg. The head was shaved and positioned in a stereotactic head holder. A 1 $cm^2$ area of skin on the dorsal surface of the skull over the right cortical hemisphere was excised and the periosteum was removed. A 4 mm diameter circular craniotomy was performed using a high speed drill (Champ-Air Dental Drill Benco Dental) over the right parietal cortex extending from attachment of the temporal muscle to midpoint of sagittal suture in the coronal direction and aligned to middle of the sagittal suture, so that the window contained some terminal branches of the middle cerebral artery. Normal saline was dripped over the cranium to avoid thermal injury of the cortex. The dura was removed and exposed brain was kept moisture with 37° C. artificial cerebrospinal fluid (CSF) solution. A 5 mm diameter coverglass was then placed over the exposed brain, and an airtight seal was produced using Nexaband Quick seal. The coverglass provided adequate mechanical protection from infection or contamination. A recovery period of four days was allowed between implantation of the cranial window and the induction of transient focal ischemia. (Ni et al. 2004) A typical closed cranial window is presented in FIG. 2A.

Middle Cerebral Artery Occlusion and Reperfusion (MCAO/R)

The animals were anesthetized with an intraperitoneal injection of Ketamine (100 mg/ml)-Xylazine (20 mg/kg) mixture (1:1) at a dose of 1 ml/kg. Body temperature was maintained at 37±5° C. by a heating lamp and heating pad. Middle cerebral artery occlusion was achieved by the intraluminal filament methods. (Hata et al. 1998) Briefly, a midline neck incision was made under the operation microscope; the right common carotid artery (CCA), external carotid artery (ECA) and internal carotid artery (ICA) were isolated. The ECA was ligated with 6-0 silk suture distal from the ICA-ECA branch and then cut distal from ligated point. Another 6-0 silk suture was tied loosely around ECA at close to the origin at the CCA. A blunted 5-0 monofilament nylon suture coated with poly-L-lysine (0.1% in deionized water, Sigma) (Belayev et al. 1999) was introduced from a small incision on ECA and then advanced into the circle of Willis, and finally to the origin of the middle cerebral artery. The silk suture around the ECA stump was tied tightly to prevent bleeding and secure the nylon suture. The nylon suture was removed after 60 minutes occlusion and ECA was permanently tied. Reperfusion was confirmed when pulsations were again observed in ICA.

A laserPro Blood Perfusion Monitor (TSI Inc) was used to monitor regional cerebral blood flow (rCBF) prior to ischemia, during MCAO and reperfusion. A 1 mm diameter microfiber laser-Doppler probe was attached to the skull 4 mm lateral and 2 mm posterior of bregma. The MCAO was considered adequate if rCBF showed a sharp drop to 25% of baseline (pre-ischemia) level, otherwise, animals were excluded. (Tsuchiya et al. 2003)

Injection of $CB_2$ Agonists in MCAO/R

The $CB_2$ agonists (O-1966 and O-3853: described in Wiley et al and WO 03/091189, incorporated herein by reference, and the copending application of Razdan et al)) were dissolved in a pure ethanol:emulphor:saline mixed solution at 1:1:18. The $CB_2$ agonists (1 mg/kg) or equal volume of vehicle were administered as an intravenous injection into the jugular vein 1 hour before MCAO or 10 minutes after reperfusion. The investigator was blinded with regard to whether the animals were members of vehicle or treatment groups during all experimental procedures and measurements.

Intravital Microscopy

The animals were anesthetized and immobilized on a plexiglass stage and secured on the microscopic stage. Intravital microscopy was performed with an epi-illuminiscence microscope (BHI Water Immersion, Olympus, Japan). A 20× water-immersion objective (WI 20, 0.4; Olympus, Tokyo, Japan), an image intensifier (Ceniisys Image Intensifier, Dage-MTI) and a monitor (12VM968; Audiotronics) were used to gain a final total magnification of 660×. Leukocytes were stained in vivo by a bolus injection of 0.05 ml of a 0.01% solution of the fluorescent dye Rhodamine 6G (Sigma, Inc) into the jugular vein. The light leaving the lamp housing was filtered to allow light with a peak wavelength of 605 nm to be transmitted to tissue. Excitation of fluorescent dyes in the leukocytes caused a shift in the wavelength of the emitted light. Selective filtering allowed visualization of the fluorescent cells on a dark background. A non-intensified black-and-white charge-coupled device (CCD) camera (CCD72, Dage-MTI) was used for visualization of the microscopic image. The image from the CCD72 camera was then displayed on the monitor, captured and recorded by a computer controlled real time TV Tuner (ATI-TV WONDER, ATI Technologies Inc) at a video frame rate of 36 frames/sec. (FIG. 2B-D) The interactions between leukocyte and endothelium were investigated offline. The investigator was blinded to drug treatment of the experimental animals when making measurement of leukocyte/endothelial interactions.

Measurement of Leukocyte/Endothelial Interactions

Leukocyte/endothelial interactions were evaluated before MCAO, 1 hour after MCAO and 24 hours after MCAO. Each vessel was exposed to the light of the microscope for 30 seconds at each viewing to minimize phototoxicity (Saetzler et al. 1997). Three venules (with diameter 30-50 μm) and three arterioles (with diameter 20-40 μm) in each animal were assessed. The number of rolling leukocytes was considered to be the total number of leukocytes moving along the endothelial cells at substantially slower velocity compared with the midstream blood cell velocity. They were counted when they passed an arbitrary line perpendicular to the longitudinal axis of the vessel over a period of 30 seconds. Adhering leukocytes were defined as the total number of the leukocytes firmly attached to the microvascular endothelium that did not change their location during the entire 30 seconds of observation period. Adhering leukocytes were scored as the number of cells per $mm^2$ of the vascular surface area, calculated from the diameter and standardized length (100 μm) of the vessel segment under investigation.

Infarct Volume Assessment

Animals were euthanized with an overdose of pentobarbital (200 mg/kg i.p) 24 hours after MCAO and then the brains were removed. The brains were chilled in ice for 10 minutes to slightly harden the tissue. Five 2 mm coronal sections were cut using a mouse brain matrix (Zivic lab).The brain sections were placed in 2% triphenyltetrazolium chloride (TTC) (Sigma, Inc) dissolved in saline and stained for 20 minutes at 37° C. in the dark. The brain sections were then fixed in 4% paraformaldehyde at 4° C. for 24 hours and the anterior and caudal face of each section was scanned by a flatbed color scanner (Microtek Inc). The resulting images were captured as JPEG files (FIG. 2E) and analyzed with NIH image software. The infarct volumes were expressed as $mm^3$ as well as the percentage of the ipsilateral hemisphere.

Neurological Evaluation

The severity of neurological deficits was evaluated 24 hours after ischemic insult using a five-point deficit score (0=normal motor function; 1=flexion of torso and of contralateral forelimb upon lifting of the animal by tail; 2=circling to the contralateral side but normal posture at rest; 3=leaning to contralateral side at rest; and 4=no spontaneous motor activity) (Hata et al. 1998).

Statistical Analysis

Numbers of leukocyte rolling on and adhering to venules or arterioles were analyzed by one-way (times) analysis of variance (ANOVA) in control group or two-way (treatments, times) ANOVA with repeated measurements followed by Bonferroni's test in treated groups. Bonferroni's test after one way ANOVA was used for analyzing differences in average of rCBF, infarct volume or neurological score. Data were presented as means±SEM. A statistically significant difference was assumed at $P<0.05$.

Results

In Vitro and In Vivo Characterization of $CB_2$ Cannabinoid Selectivity

The affinity of O-1966 for $CB_1$ and $CB_2$ cannabinoid receptors was reported previously to be 5,055±984 and 23±2.1 nM, respectively(Wiley et al. 2002). We report herein that it stimulated $^{35}S$-GTPγS binding with a EC50 of 70±14 nM and an Emax of 74±5 (percent of maximal stimulation produced by the full agonist CP 55,940). O-3853 binds to $CB_1$ and $CB_2$ receptors with respective affinities of 815 f 127 and 17.3±2.5 nM. It was also effective in stimulating $^{35}S$-GTPγS binding with an EC50 of 6.0±2.5 nM and an Emax of 87±5%, whereas its ability for stimulating $CB_1$ $^{35}S$-GTPγS was very low (EC50=1509±148 and Emax of 43±3%). I.v. administration of O-1966 to mice failed to produce effects in the tetrad test (the measurements for locomotor activity, analgesia, body temperature, and catalepsy) in doses up to 30 mg/kg, consistent with its very low $CB_1$ receptor affinity.

Intravenous administration of O-3853 to mice resulted in weak activity in two of the tetrad measures. It depressed spontaneous activity and blocked tail-flick response with ED50's (confidence limits) of 10.3 (6.2-17.0) and 11.4 (8.2-16.0) mg/kg. It failed to either alter body temperature or produce catalepsy up to doses of 30 mg/kg. The ED50's of the $CB_1$/$CB_2$ cannabinoid receptor agonist $\Delta^9$-tetrahydrocannabinol are approximately 1-2 mg/kg in these four measures.

$CB_2$ Agonists Did not Change the rCBF During MCAO

During MCAO, rCBF decreased to approximately 25% of baseline value. Administration of the $CB_2$ agonists (O-3853 or O-1966) 1 hour prior to occlusion at a dose of 1 mg/kg had no effect on rCBF during the 1 hour occlusion period when compared with the vehicle-treated group (FIG. 3).

Effects of $CB_2$ Agonists on Cerebral Infarction

Administration of $CB_2$ agonists (O-3853 or O-1966) at either 1 hour before MCAO (pre-ischemic treatment) or 10 minutes after reperfusion (post-reperfusion treatment) significantly reduced the cerebral infarction compared with vehicle-treated group. Infarct volumes were similar in pre-ischemic treated controls (99.2±6.9 $mm^3$, 34±2.3%) and in post-reperfusion treated controls (99.8±4.6 $mm^3$, 38±1.6%). Administration of O-3853 prior to ischemia reduced infarct size to 68.2±5.0 $mm^3$ and 24±2.4%. Furthermore, administration of O-3853 after reperfusion reduced infarct size to 71.9±6.1 $mm^3$ and 28±1.3%. Likewise, O-1966 reduced infarct size to 65.6±4.0 $mm^3$, 25±2.5%; and 71.3±5.5 $mm^3$, 27±2% when administered either before ischemia (FIG. 5A) or after reperfusion (FIG. 5B), respectively.

Effects of $CB_2$ Agonists on Neurological Function

Administration of the $CB_2$ agonists (O-3853 or O-1966) at either 1 hour before MCAO (pretreatment) or during reperfusion significantly improved the motor function at 24 hours post-ischemia. (FIG. 7) Motor function score in animals receiving vehicle prior to MCAO was 3.25±0.20 which was reduced to 2.04±0.18 with O-3853 pretreatment and 1.69±0.30 with O-1966 pretreatment.

MCAO Enhanced Leukocyte/Endothelial Interactions

Leukocyte rolling and adhesion on both venules and arterioles were significantly enhanced during 1 hour MCAO followed by 23 hours reperfusion. Leukocyte rolling on venules increased from 3±0.2 (before MCAO) to 6.9±0.8 (1 hour after MCAO) and 8.9±0.8 (24 hours after MCAO); leukocyte adhesion on venules increased from 18±8.5 (before MCAO) to 134.7±30.9 (1 hour after MCAO) and 163±25 (24 hours after MCAO); leukocyte rolling on arterioles increased from 0.2±0.2 (before MCAO) to 1.7±0.6 (24 hours after MCAO); leukocyte adhesion on arterioles increased from 0 (before MCAO) to 196±54.7 (1 hour after MCAO) and 160±21.9 (24 hours after MCAO) (FIG. 8).

Effects of $CB_2$ Agonists on Leukocyte/Endothelial Interactions During Cerebral Ischemia/Reperfusion Injury Treatment with either of the $CB_2$ agonists 1 hour prior to MCAO attenuated leukocyte/endothelial interactions during cerebral ischemia/reperfusion injury. Both $CB_2$ agonists significantly decreased leukocyte rolling and adhesion on venules 1 hour after ischemia and following 23 hours of reperfusion. Leukocyte adhesion to arterioles was also attenuated by both agonists during both measurement periods following ischemia. Although both agents reduced leukocyte rolling along arterioles 24 hours after MCAO, there was no difference in leukocyte rolling as a result of treatment 1 hour after MCAO. (FIG. 9).

The closed cranial window technique was utilized to evaluate the effect of selective $CB_2$ agonists on endothelial/leukocyte interactions. Before ischemia, baseline leukocyte rolling and adhesion on venules was very low and there were almost no leukocyte/endothelial interactions on arterioles because of high shear stress. One hour after ischemia, there was a significant increase in leukocytes rolling on venules.

The lack of increase in leukocyte rolling in arterioles during the first hour of reperfusion was probably the result of an increase in shear rate resulting from the ischemia induced reactive hyperemia. The increased leukocyte/endothelial interactions that resulted from ischemia/reperfusion injury were dramatically diminished by both $CB_2$ agonists. Since leukocytes rolling and adhesion on endothelial cells are critical steps for their full activation and extravasation into brain tissue to participate in the inflammatory response (Heinel et al. 1994), it is possible that $CB_2$ activation exerts at least part of its neuroprotective effects via modulation of white cell contributions to inflammatory reactions during ischemia/reperfusion injury.

While it is likely that the attenuation of leukocyte rolling and adhesion following stroke is directly caused by $CB_2$ receptor activation on these cells, it is also possible that the attenuation of rolling and adhesion is not a direct contributory mechanism but rather a reflection of a decrease in damage due to $CB_2$ receptor activation in other cells such as microglia.

In a previous study using selective $CB_1$ and $CB_2$ antagonists, we found WIN55212-2, exerted its neuroprotective effects in a mouse EAE model via $CB_2$ not $CB_1$ activation, and that this neuroprotective effect was also associated with an attenuation of leukocyte/endothelial cell interactions. (Ni et al. 2004)

In addition to modulating inflammatory responses through inhibition of leukocyte/endothelial adhesion, a number of laboratories have also reported that the $CB_2$ receptors also exist on microglial cells and that $CB_2$ receptors were highly up-regulated by inflammatory stimulation in microglia (Maresz et al. 2005; Nunez et al. 2004). Activated microglia play an active role in cerebral ischemia/reperfusion injury, through phagocytic activity, inflammatory cytokine production and the release of destructive proteolytic enzymes as well as neurotoxin secretion (Mabuchi et al. 2000; Schilling et al. 2005). It is therefore possible that the beneficial effects of $CB_2$ agonist treatment in stroke may result in part from inhibition of microglial activation.

Another possible mechanism through which $CB_2$ receptor agonists could exert a protective effect is by modulating cerebral blood flow through alterations in cerebral vascular resistance. However rCBF during ischemia was not changed by the agonists in the model used in this investigation. Therefore it seems unlikely that $CB_2$ activation exerts its protective effects by influencing cerebral vascular resistance during ischemia. Since transient MCAO should result in maximal vasodilation early in the reperfusion period, it is also unlikely that vasodilation caused by the $CB_2$ agonists during this time period is a contributing factor.

Effect of $CB_2$ Agonists in Spinal Cord Injury.

A thoracic spinal cord injury model was induced in female 6-8 week old C57BL/6 mice. Spinal cord $CB_2$ mRNA expression was evaluated in sham animals and SCI animals 24 hours after injury by real time RT-PCR. Animals were randomized into two groups: the experimental group received intraperitoneal injections of a selective $CB_2$ agonist (O-1966; 1 mg/kg) one hour before injury, 24 and 48 hours after injury; the control group received equal volumes of vehicle. Both groups were tested for motor function by using the Basso Mouse Scale for Locomotion (BMS) and the Basso, Beattie, Bresnahan Locomotor Rating Scale (BBB) on post-procedure days 1, 7, and 14. Urine mass was recorded twice daily to assess bladder recovery. The inflammatory cytokine TNF-α was measured by real time RT-PCR in both groups 24 hours after SCI.

Results:

$CB_2$ expression in spinal cord increased dramatically after injury (see FIG. 11). Animals treated with the received $CB_2$ agonist treatment demonstrated better motor function recovery than the control group at all evaluation times after injury (See FIG. 12). The $CB_2$ agonist treated group also had significantly improved bladder function recovery rate (45%) than the control group (14%) $14^{th}$ days after SCI (FIG. 13). Administration of the $CB_2$ agonist also decreased TNF-α expression in the injured spinal cord compared to control group (FIG. 14).

These results indicate that $CB_2$ agonist administration improved motor and autonomic function in a mouse model of SCI. The improvement may be mediated by the attenuation of inflammation in spinal cord after injury.

REFERENCES

Belayev L, Busto R, Zhao W, Fernandez G, Ginsberg M D. (1999) Middle cerebral artery occlusion in the mouse by intraluminal suture coated with poly-L-lysine: neurological and histological validation. *Brain Res* 833:181-190

Berdyshev E V. (2000) Cannabinoid receptors and the regulation of immune response. *Chem Phys Lipids* 108: 169-190

Connolly E S, Jr., Winfree C J, Springer T A, Naka Y, Liao H, Yan S D, Stern D M, Solomon R A, Gutierrez-Ramos J C, Pinsky D J. (1996) Cerebral protection in homozygous null ICAM-1 mice after middle cerebral artery occlusion. Role of neutrophil adhesion in the pathogenesis of stroke. *J Clin Invest* 97:209-216

Croxford J L. (2003) Therapeutic potential of cannabinoids in CNS disease. *CNS Drugs* 17:179-202

Danton G H, Dietrich W D. (2003) Inflammatory mechanisms after ischemia and stroke. *J Neuropathol Exp Neurol* 62:127-136

Grundy R I. (2002) The therapeutic potential of the cannabinoids in neuroprotection. *Expert Opin Investig Drugs* 11:1365-1374

Grundy R I, Rabuffetti M, Beltramo M. (2001) Cannabinoids and neuroprotection. *Mol Neurobiol* 24:29-51

Hata R, Mies G, Wiessner C, Fritze K, Hesselbarth D, Brinker G, Hossmann K A. (1998) A reproducible model of middle cerebral artery occlusion in mice: hemodynamic, biochemical, and magnetic resonance imaging. *J Cereb Blood Flow Metab* 18:367-375

Hayakawa K, Mishima K, Abe K, Hasebe N, Takamatsu F, Yasuda H, Ikeda T, Inui K, Egashira N, Iwasaki K, Fujiwara M. (2004) Cannabidiol prevents infarction via the non-CB1 cannabinoid receptor mechanism. *Neuroreport* 15:2381-2385

Heinel L A, Rubin S, Rosenwasser R H, Vasthare U S, Tuma R F. (1994) Leukocyte involvement in cerebral infarct generation after ischemia and reperfusion. *Brain Res Bull* 34:137-141

Iadecola C, Alexander M. (2001) Cerebral ischemia and inflammation. *Curr Opin Neurol* 14:89-94

Jackson S J, Diemel L T, Pryce G, Baker D. (2005) Cannabinoids and neuroprotection in CNS inflammatory disease. *J Neurol Sci* 233:21-25

Kataoka H, Kim S W, Plesnila N. (2004) Leukocyte-endothelium interactions during permanent focal cerebral ischemia in mice. *J Cereb Blood Flow Metab* 24:668-676

Kishimoto T K, Rothlein R. (1994) Integrins, ICAMs, and selectins: role and regulation of adhesion molecules in neutrophil recruitment to inflammatory sites. *Adv Pharmacol* 25:117-169

Klein T W, Gabral G. (2006) Cannabinoid-Induced Immune Suppression and Modulation of Antigen-Presenting Cells. *J Neuroimmune Pharmacol* 1:50-64

Klein T W, Newton C A, Friedman H. (2001) Cannabinoids and the immune system. *Pain Res Manag* 6:95-101

Mabuchi T, Kitagawa K, Ohtsuki T, Kuwabara K, Yagita Y, Yanagihara T, Hori M, Matsumoto M. (2000) Contribution of microglia/macrophages to expansion of infarction and response of oligodendrocytes after focal cerebral ischemia in rats. *Stroke* 31:1735-1743

Maier C M, Hsieh L, Yu F, Bracci P, Chan P H. (2004) Matrix metalloproteinase-9 and myeloperoxidase expression: quantitative analysis by antigen immunohistochemistry in a model of transient focal cerebral ischemia. *Stroke* 35:1169-1174

Maresz K, Carrier E J, Ponomarev E D, Hillard C J, Dittel B N. (2005) Modulation of the cannabinoid CB2 receptor in microglial cells in response to inflammatory stimuli. *J Neurochem* 95:437-445

Martin B R, Jefferson R G, Winckler R, Wiley J L, Thomas B F, Crocker P J, Williams W, Razdan R K. (2002)

Assessment of structural commonality between tetrahydrocannabinol and anandamide. *Eur J Pharmacol* 435: 35-42

Mishima K, Hayakawa K, Abe K, Ikeda T, Egashira N, Iwasaki K, Fujiwara M. (2005) Cannabidiol prevents cerebral infarction via a serotonergic 5-hydroxytryptamine1A receptor-dependent mechanism. *Stroke* 36:1077-1082

Muthian S, Rademacher D J, Roelke C T, Gross G J, Hillard C J. (2004) Anandamide content is increased and CB1 cannabinoid receptor blockade is protective during transient, focal cerebral ischemia. *Neuroscience* 129:743-750

Nagayama T, Sinor A D, Simon R P, Chen J, Graham S H, Jin K, Greenberg D A. (1999) Cannabinoids and neuroprotection in global and focal cerebral ischemia and in neuronal cultures. *J Neurosci* 19:2987-2995

Ni X, Geller E B, Eppihimer M J, Eisenstein T K, Adler M W, Tuma R F. (2004) Win 55212-2, a cannabinoid receptor agonist, attenuates leukocyte/endothelial interactions in an experimental autoimmune encephalomyelitis model. *Mult Scler* 10:158-164

Nunez E, Benito C, Pazos M R, Barbachano A, Fajardo O, Gonzalez S, Tolon R M, Romero J. (2004) Cannabinoid CB2 receptors are expressed by perivascular microglial cells in the human brain: an immunohistochemical study. *Synapse* 53:208-213

Parmentier-Batteur S, Jin K, Mao X O, Xie L, Greenberg D A. (2002) Increased severity of stroke in CB1 cannabinoid receptor knock-out mice. *J Neurosci* 22:9771-9775

Pertwee R G. (1999) Pharmacology of cannabinoid receptor ligands. *Curr Med Chem* 6:635-664

Rodriguez de Fonseca F, Del Arco I, Bermudez-Silva F J, Bilbao A, Cippitelli A, Navarro M. (2005) The endocannabinoid system: physiology and pharmacology. *Alcohol Alcohol* 40:2-14

Saetzler R K, Jallo J, Lehr H A, Philips C M, Vasthare U, Arfors K E, Tuma R F. (1997) Intravital fluorescence microscopy: impact of light-induced phototoxicity on adhesion of fluorescently labeled leukocytes. *J Histochem Cytochem* 45:505-513

Schilling M, Besselmann M, Muller M, Strecker J K, Ringelstein E B, Kiefer R. (2005) Predominant phagocytic activity of resident microglia over hematogenous macrophages following transient focal cerebral ischemia: an investigation using green fluorescent protein transgenic bone marrow chimeric mice. *Exp Neurol* 196:290-297

Schwenkreis P, Tegenthoff M. (2003) [Therapeutic use of cannabinoids in neurology]. *Schmerz* 17:367-373

Sughrue M E, Mehra A, Connolly E S, Jr., D'Ambrosio A L. (2004) Anti-adhesion molecule strategies as potential neuroprotective agents in cerebral ischemia: a critical review of the literature. *Inflamm Res* 53:497-508

Tsuchiya D, Hong S, Kayama T, Panter S S, Weinstein P R. (2003) Effect of suture size and carotid clip application upon blood flow and infarct volume after permanent and temporary middle cerebral artery occlusion in mice. *Brain Res* 970:131-139

Vasthare U S, Heinel L A, Rosenwasser R H, Tuma R F. (1990) Leukocyte involvement in cerebral ischemia and reperfusion injury. *Surg Neurol* 33:261-265

Walter L, Stella N. (2004) Cannabinoids and neuroinflammation. *Br J Pharmacol* 141:775-785

Weaver M, Leshley K, Sands H, Gritman K R, Legos J J, Tuma R F. (2002) LEX032, a novel recombinant serpin, protects the brain after transient focal ischemia. *Microvasc Res* 63:327-334

White B C, Sullivan J M, DeGracia D J, O'Neil B J, Neumar R W, Grossman L I, Rafols J A, Krause G S. (2000) Brain ischemia and reperfusion: molecular mechanisms of neuronal injury. *J Neurol Sci* 179:1-33

Wiley J L, Beletskaya I D, Ng E W, Dai Z, Crocker P J, Mahadevan A, Razdan R K, Martin B R. (2002) Resorcinol derivatives: a novel template for the development of cannabinoid CB(1)/CB(2) and CB(2)-selective agonists. *J Pharmacol Exp Ther* 301:679-689

Wood P L. (2003) *Neuroinflammation: mechanisms and management.* Totowa, N.J.: Humana Press

The invention claimed is:

1. A method of treating cerebral ischemia/reperfusion injury or spinal cord injury in a patient in need thereof or preventing spinal cord injury in a patient, comprising administering to the patient a therapeutically effective amount of a cannabinoid $CB_2$ receptor agonist, wherein the agonist is O-1966.

2. The method as claimed in claim 1, wherein the patient suffers from a disease selected from the group consisting of head trauma, stroke, cerebral bleeds, Alzheimer's and Parkinson's diseases and CNS inflammation in multiple sclerosis.

3. The method as claimed in claim 1, wherein the agonist is administered in combination with a $CB_1$ receptor antagonist.

4. A pharmaceutical composition for cerebral ischemia/reperfusion injury or spinal cord injury in a patient in need thereof after the cerebral ischemia/reperfusion injury or spinal cord injury, comprising a therapeutically effective amount of a cannabinoid $CB_2$ receptor agonist, wherein the agonist is O-1966.

* * * * *